(12) United States Patent
An

(10) Patent No.: US 12,102,811 B2
(45) Date of Patent: Oct. 1, 2024

(54) MEDICINE INJECTING TIP, HAND PIECE, AND SKIN TREATING DEVICE

(71) Applicant: JEISYS MEDICAL INC., Seoul (KR)

(72) Inventor: Kyoung Ho An, Seoul (KR)

(73) Assignee: Jeisys Medical Inc., Seoul (KR)

( * ) Notice: Subject to any disclaimer, the term of this patent is extended or adjusted under 35 U.S.C. 154(b) by 0 days.

(21) Appl. No.: 17/826,737

(22) Filed: May 27, 2022

(65) Prior Publication Data
US 2022/0288327 A1   Sep. 15, 2022

Related U.S. Application Data

(63) Continuation of application No. 16/697,163, filed on Nov. 26, 2019, now Pat. No. 11,376,374, which is a
(Continued)

(30) Foreign Application Priority Data

Jul. 2, 2018 (KR) .................. 10-2018-0076601
Dec. 4, 2018 (KR) .................. 10-2018-0154688

(51) Int. Cl.
*A61M 5/42* (2006.01)
*A61M 5/142* (2006.01)
(Continued)

(52) U.S. Cl.
CPC ........ *A61M 5/425* (2013.01); *A61M 5/14216* (2013.01); *A61M 5/3148* (2013.01);
(Continued)

(58) Field of Classification Search
CPC .............. A61M 5/425; A61M 5/14216; A61M 5/3148; A61M 5/3286; A61M 5/46;
(Continued)

(56) References Cited

U.S. PATENT DOCUMENTS 6,743,211 B1   6/2004 Prausnitz et al.
11,376,374 B2 *  7/2022 An ..................... A61N 1/0504
(Continued)

FOREIGN PATENT DOCUMENTS

EP   2893894      7/2015
EP   2893894 A2   7/2015
(Continued)

OTHER PUBLICATIONS

An Office Action; "Notice of Reasons for Refusal", mailed by the Japanese Patent Office on Jan. 25, 2022, which corresponds to Japanese Patent Application No. 2020-573399 and is related to U.S. Appl. No. 16/697,163.
(Continued)

*Primary Examiner* — James D Ponton
(74) *Attorney, Agent, or Firm* — Leydig, Voit & Mayer, Ltd.

(57) ABSTRACT

Provided are a medicine injecting tip, which injects a medicine into a hole in a skin formed by a needle while invading the needle to a preset depth of a deep portion of the skin, a hand piece equipped with the medicine injecting tip, and a skin treatment device using the medicine injecting tip. The medicine injecting tip includes a cylinder, a plunger that reciprocates downward and upward, and has a first space and a second space formed inside the cylinder, and a needle disposed in the plunger and disposed in the second space of the cylinder. The needle is inserted into a skin and a negative pressure state is formed in the second space when the plunger moves downward, and the needle is discharged from the skin and a positive pressure state is formed in the second space, when the plunger moves upward.

20 Claims, 12 Drawing Sheets

Related U.S. Application Data continuation of application No. PCT/KR2019/007319, filed on Jun. 18, 2019.

(51) Int. Cl.
   *A61M 5/31*   (2006.01)
   *A61M 5/32*   (2006.01)
   *A61M 5/46*   (2006.01)
   *A61N 1/05*   (2006.01)
   *A61N 1/06*   (2006.01)

(52) U.S. Cl.
   CPC ............ *A61M 5/3286* (2013.01); *A61M 5/46* (2013.01); *A61N 1/0502* (2013.01); *A61N 1/0504* (2013.01); *A61N 1/06* (2013.01)

(58) Field of Classification Search
   CPC ........ A61M 2037/0023; A61M 5/3298; A61M 37/0015; A61M 2037/0007; A61M 5/158; A61M 5/32; A61M 37/00; A61N 1/0502; A61N 1/0504; A61N 1/06; A61N 1/328; A61N 1/322; A61N 1/08; A61N 1/36017; A61B 2018/00994; A61B 18/1477; A61B 2018/0047; A61B 2018/143
   See application file for complete search history.

(56) References Cited

U.S. PATENT DOCUMENTS

| | | | |
|---|---|---|---|
| 2005/0137525 A1* | 6/2005 | Wang ................ | A61M 37/0015 604/93.01 |
| 2009/0036795 A1 | 2/2009 | Duineveld | |
| 2009/0099503 A1* | 4/2009 | Mitsuda ................. | A61P 17/10 604/25 |
| 2011/0092884 A1* | 4/2011 | Kang ..................... | A61B 18/14 604/21 |
| 2013/0041265 A1 | 2/2013 | Sostek et al. | |
| 2015/0258270 A1 | 9/2015 | Kuni | |
| 2016/0199581 A1 | 7/2016 | Cachemaille | |

FOREIGN PATENT DOCUMENTS

| | | |
|---|---|---|
| JP | 2000-287992 A | 10/2000 |
| JP | 2011-083347 A | 4/2011 |
| JP | 2015-528345 A | 9/2015 |
| KR | 10-0532671 B1 | 12/2005 |
| KR | 10-1286752 B1 | 7/2013 |
| KR | 10-1596716 B1 | 2/2016 |
| KR | 10-2017-0014482 A | 2/2017 |
| KR | 1020170058162 | 5/2017 |
| KR | 101745445 | 6/2017 |
| KR | 101763287 | 8/2017 |
| WO | 9423777 | 10/1994 |

OTHER PUBLICATIONS

International Search Report issued in PCT/KR2019/007319; mailed Sep. 18, 2019.

Extended European Search Report issued in EP 19 82 9896.0-1122 by the European Patent Office on Mar. 14, 2022, which is related to International Patent Application No. PCT/KR2019/007319.

* cited by examiner

FIG. 12

S100
Move downward needle electrode and plunger and form vacuum sate in second space of cylinder

S200
Apply high frequency to deep portion of skin by needle electrode

S300
Move upward needle electrode and plunger and form positive pressure state in second space of cylinder

MEDICINE INJECTING TIP, HAND PIECE, AND SKIN TREATING DEVICE

CROSS-REFERENCE TO RELATED APPLICATIONS

The present application is a continuation of U.S. patent application Ser. No. 16/697,163, filed on Nov. 26, 2019, which is a continuation of International Patent Application No. PCT/KR2019/007319, filed Jun. 18, 2019, which is based upon and claims the benefit of priority to Korean Patent Application Nos. 10-2018-0076601 and 10-2018-0154688, filed on Jul. 2, 2018 and Dec. 4, 2018. The disclosures of the above-listed applications are hereby incorporated by reference herein in their entirety.

BACKGROUND

Embodiments of the inventive concept described herein relate to a medicine injecting tip, a hand piece, and a skin treating device, capable of invading a needle to a preset depth of a deep portion of a skin due to a pumping effect while injecting a medicine into an invaded part.

Recently, a skin treating device has been developed for scar treatment, hair growth treatment, osmidrosis treatment, vascular treatment, fat reduction, wrinkle removal, skin elasticity recovery, sebum removal, and acne treatment. The skin treating device repeatedly invades a plurality of needles into a skin to remove a malignant tissue and to form a new tissue, thereby treat the skin of a target person.

Further, although not essential, a high frequency may be applied to a plurality of needles (in this case, electrical energy may be applied to the needles in various manners without limitation to the high frequency; meanwhile, in this case, the plurality of needles may be called radio frequency (RF) needle electrodes).

A device employing a manner of transmitting a high frequency to a skin tissue invades an RF needle electrode to a deep portion (for example, a derma layer) of the skin at a target point (for example, a face) by using a hand piece having a single or a plurality of RF needle electrodes, removes damaged collagen or elastic fiber from the deep portion of the skin at the target point and accelerates the regeneration of collagen or elastic fiber by using heat generated by the high frequency. Furthermore, these skin treatment devices improve the pigmentation of the skin, acne marks, and wrinkles.

In this case, when a cutting edge of an end portion of a single or a plurality of RF needle electrodes is exposed and remaining portions of the RF needle electrodes are coated with an insulating material, a high frequency may be intensively transmitted to the deep portion of the skin (see FIGS. 1A and 1B; FIG. 1A illustrates the case that a needle electrode is not coated with an insulating material, and FIG. 1B illustrates the case that a needle electrode is coated with an insulating material).

However, a dent having a predetermined curvature or a wrinkle is formed on the surface of the skin at the target point due to the pressure in the treatment. Accordingly, a plurality of needles may not be invaded to a uniform depth. In other words, some of the plurality of needles fails to reach the deep portion of the skin at the target point, which causes a skin regeneration efficiency to be lowered.

Meanwhile, in the procedure of regenerating a skin using a plurality of needles, a medicine is applied to relieve pain or treat a fine wound caused when the plurality of needles are invaded into the deep portion of the skin.

In this case, it is effective to deeply inject a medicine into the invaded part so as to improve the efficiency of the medicine. However, it may be difficult for a typical skin treating device to deeply inject the medicine into the invaded part.

SUMMARY

Embodiments of the inventive concept provide a medicine injecting tip capable of injecting a medicine into a hole in a skin formed by a needle while invading the needle to a preset depth of a deep portion of the skin, a hand piece equipped with the medicine injecting tip, and a skin treatment device using the medicine injecting tip.

The objects of the inventive concept are not limited to the above, but other effects, which are not mentioned, will be apparently understood to those skilled in the art.

According to an exemplary embodiment, a medicine injecting tip may include a cylinder, a plunger reciprocating downward and upward, and having a first space and a second space formed inside the cylinder, and a needle disposed in the plunger and disposed in the second space of the cylinder. The needle may be inserted into a skin when the plunger moves downward. The needle may be discharged from the skin and a positive pressure state is formed in the second space, when the plunger moves upward.

A hole may be formed in the skin as the needle is inserted into the skin and discharged from the skin, and a medicine may be injected into the hole, which is formed in the skin, when the second space is in the positive pressure state.

A negative pressure state may be formed in the second space when the plunger moves downward.

A surface of the skin may be pulled to the second space due to the negative pressure state of the second space such that the needle is invaded to a preset depth.

A first channel may be formed in the medicine injecting tip to connect the first space with the second space.

The first channel may be at least one of a fluid passage formed in the plunger, a gap between the cylinder and the plunger, and a tube connecting the first space with the second space.

As a variation in a volume of the first space is greater than a variation in a volume of the second space when the plunger reciprocates, a gas in the second space may move into the first space through the first channel when the plunger moves downward, and gas in the first space may move into the second space through the first channel when the plunger moves upward.

A valve may be disposed in the cylinder to connect an outside with the first space in an open state.

The valve may be open in the negative pressure state of the first space to introduce external air into the first space, and is closed in the positive pressure state of the first space to block air in the first space from leaking to the outside.

The valve may be open when the plunger moves downward, and is closed when the plunger moves upward.

The cylinder may include a first cylinder and a second cylinder, the plunger may include a first plunger forms the first space and a redundant space in the first cylinder, and a second plunger may form the second space in the second cylinder, and a second channel may be formed in the first cylinder to connect the redundant space with the outside.

A third channel may be formed in the first plunger to connect the redundant space with the outside.

A fourth channel may be formed in the cylinder to connect the first space with the outside.

The fourth channel is open due to movement of the plunger when the plunger moves downward, and is closed due to the movement of the plunger when the plunger moves upward.

A fifth channel may be formed in the cylinder to connect the first space with the outside.

The fifth channel may be open due to movement of the plunger when the plunger moves downward, and may be closed due to the movement of the plunger when the plunger moves upward.

A high frequency may be applied to the needle.

The high frequency applied to the needle generates thermal energy in a deep portion of the skin.

According to an exemplary embodiment, a hand piece may be mounted on the medicine injecting tip.

According to an exemplary embodiment, a skin treating device may inject a medicine into a deep portion of a skin of a patient using the medicine injecting tip.

BRIEF DESCRIPTION OF THE FIGURES

The above and other objects and features will become apparent from the following description with reference to the following figures, wherein like reference numerals refer to like parts throughout the various figures unless otherwise specified, and wherein:

FIG. 12 is a flowchart illustrating a method for treating a skin using a medicine injecting tip according to the inventive concept.

DETAILED DESCRIPTION

Figure 1A:
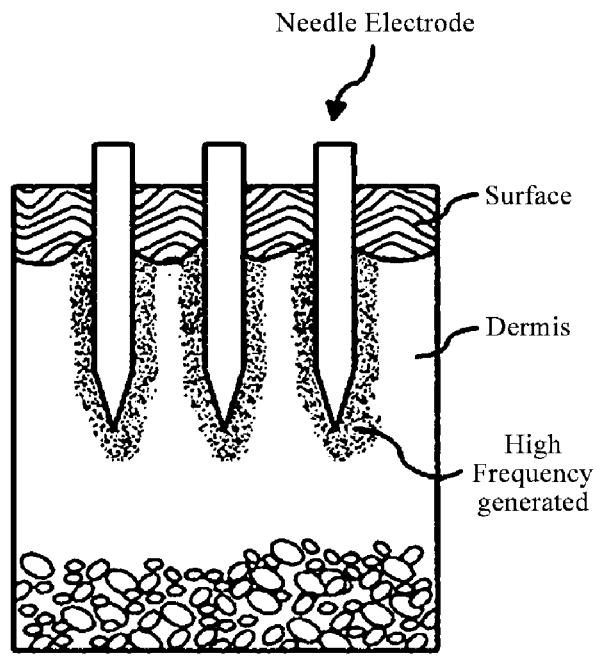
FIGS. 1A and 1B are schematic views illustrating that a high frequency is applied using RF needles.

Advantage points and features of the inventive concept and a method of accomplishing thereof will become apparent from the following description with reference to the following figures, wherein embodiments will be described in detail with reference to the accompanying drawings. However, the inventive concept may be embodied in various different forms, and should not be construed as being limited only to the illustrated embodiments. Rather, these embodiments are provided as examples so that this disclosure will be thorough and complete, and will fully convey the concept of the inventive concept to those skilled in the art. The inventive concept may be defined by scope of the claims.

The terminology used in the inventive concept is provided for the illustrative purpose, but the inventive concept is not limited thereto. As used herein, the singular terms "a," "an" and "the" are intended to include the plural forms as well, unless the context clearly indicates otherwise. Furthermore, it will be further understood that the terms "comprises", "comprising," "includes" and/or "including", when used herein, specify the presence of stated components, but do not preclude the presence or addition of one or more other components. The same reference numerals will be assigned to the same component throughout the whole specification, and "and/or" refers to that components described include not only individual components, but at least one combination of the components. It will be understood that, although the terms "first", "second", etc., may be used herein to describe various components, these components should not be limited by these terms. These terms are only used to distinguish one component from another component. Thus, a first component to be described below may be a second component without departing from the teachings of the inventive concept.

Unless otherwise defined, all terms (including technical and scientific terms) used herein have the same meaning as commonly understood by those skilled in the art. It will be further understood that terms, such as those defined in commonly used dictionaries, should be interpreted as having a meaning in other words consistent with their meaning in the context of the relevant art and will not be interpreted in an idealized or overly formal sense unless expressly so defined herein.

Spatially relative terms, such as "below", "beneath", "lower", "above", "upper", and the like, may be used herein for ease of description to describe one component or feature's relationship to another component(s) or feature(s) as illustrated in accompanying drawings. It will be understood that the spatially relative terms are intended to encompass different orientations of the components in use or operation in addition to the orientation depicted in the drawings. For example, when a component illustrated in accompanying drawings is reversed, a component provided 'below' or 'beneath' another component may be placed 'above' another component. Accordingly, the term "below" may include both concepts of "below" and "above. A component may be oriented in a different direction. Accordingly, terminology having relatively spatial concepts may be variously interpreted depending on orientations.

Figure 1B:
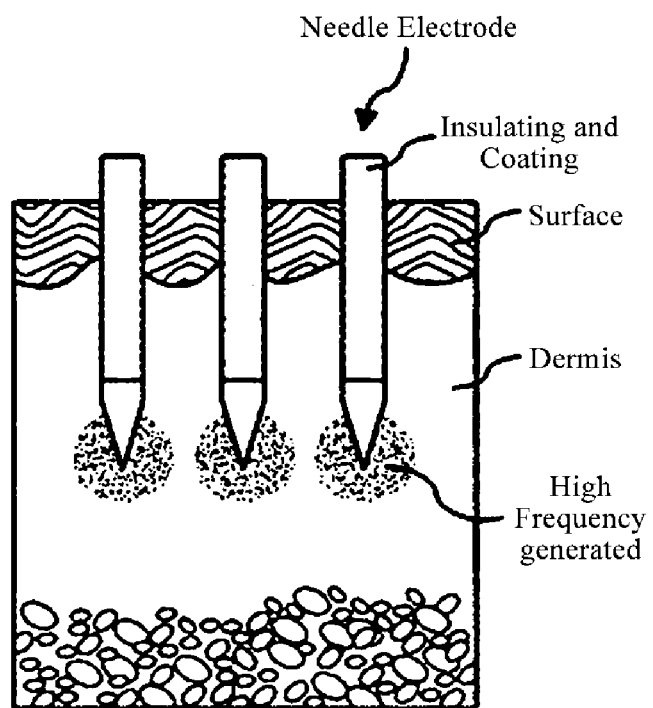
Figure 2:
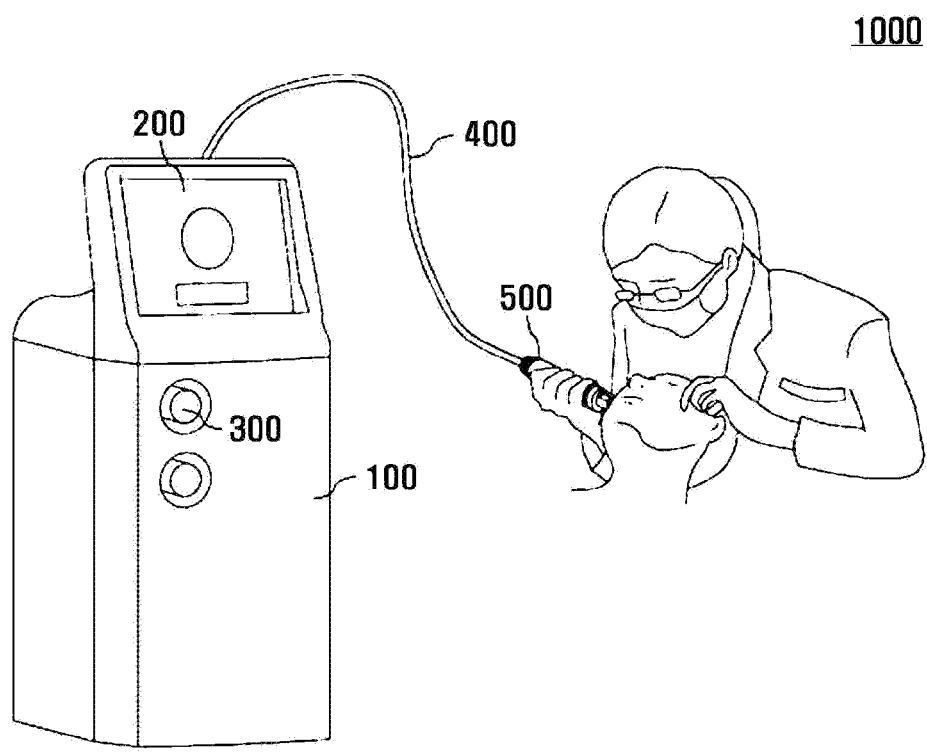
FIG. 2 is a perspective view illustrating a skin treating device, according to the inventive concept.
Figure 3:
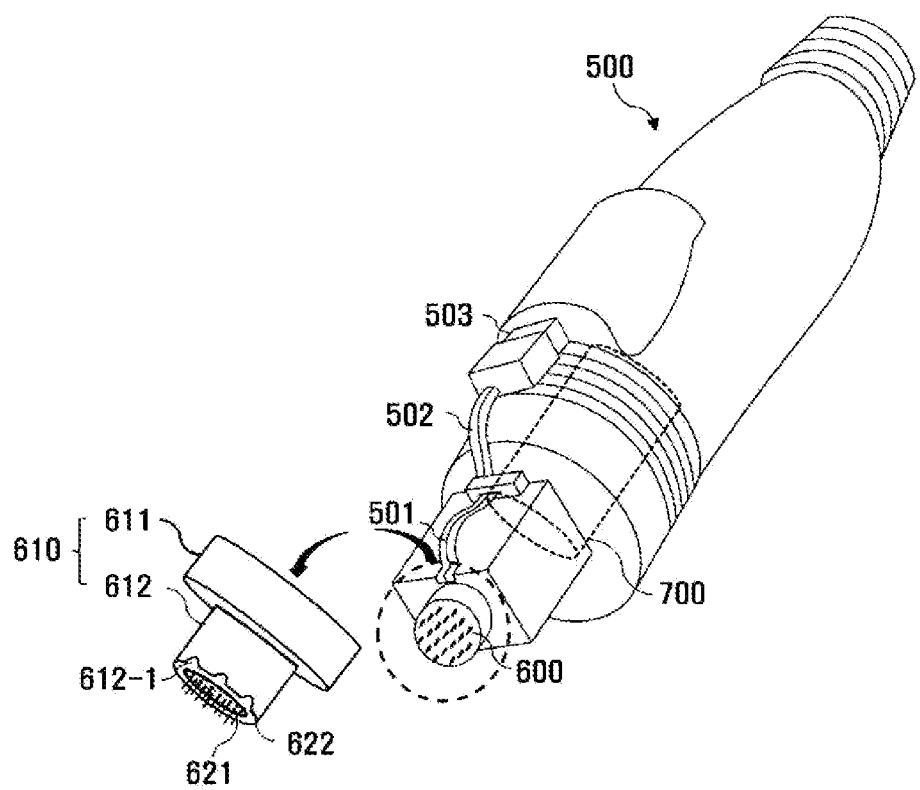
FIG. 3 is a perspective view illustrating a hand piece, according to the inventive concept.
Figure 4:
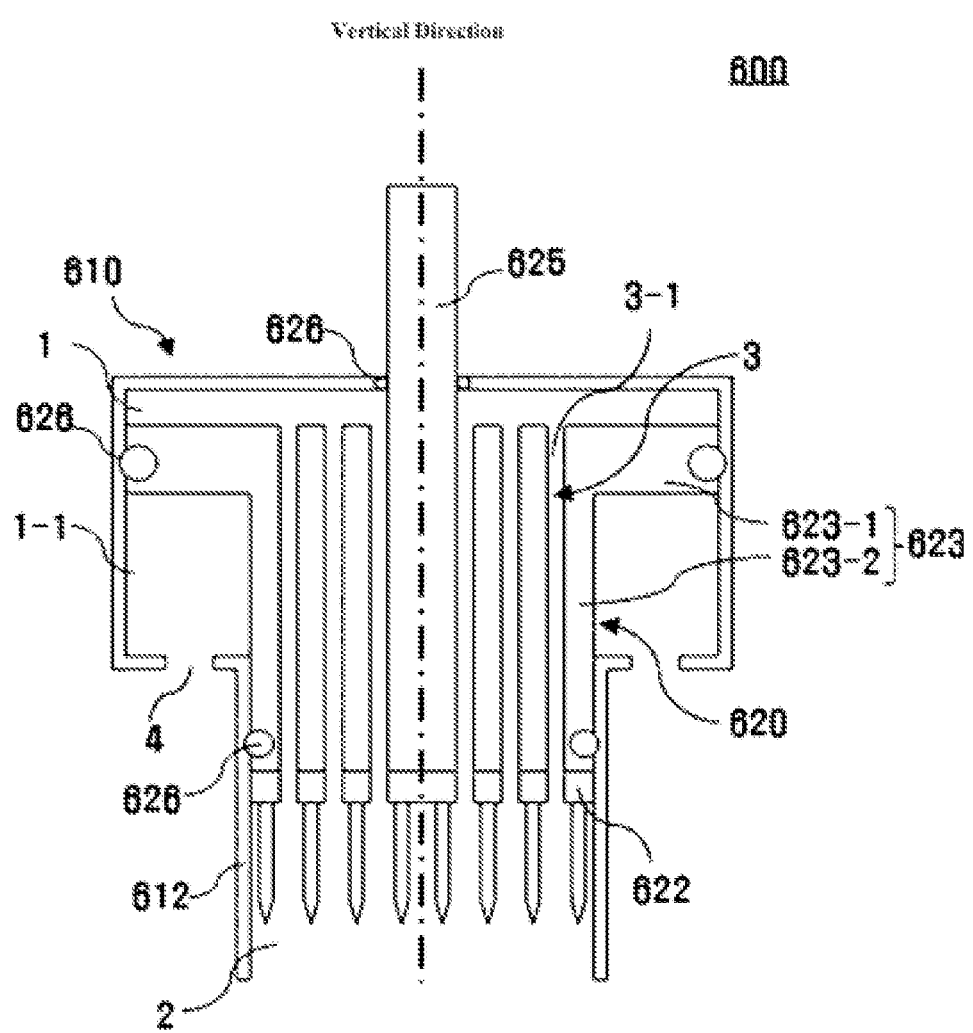
FIG. 4 is a sectional view illustrating a medicine injecting tip, according to the inventive concept.
Figure 5:
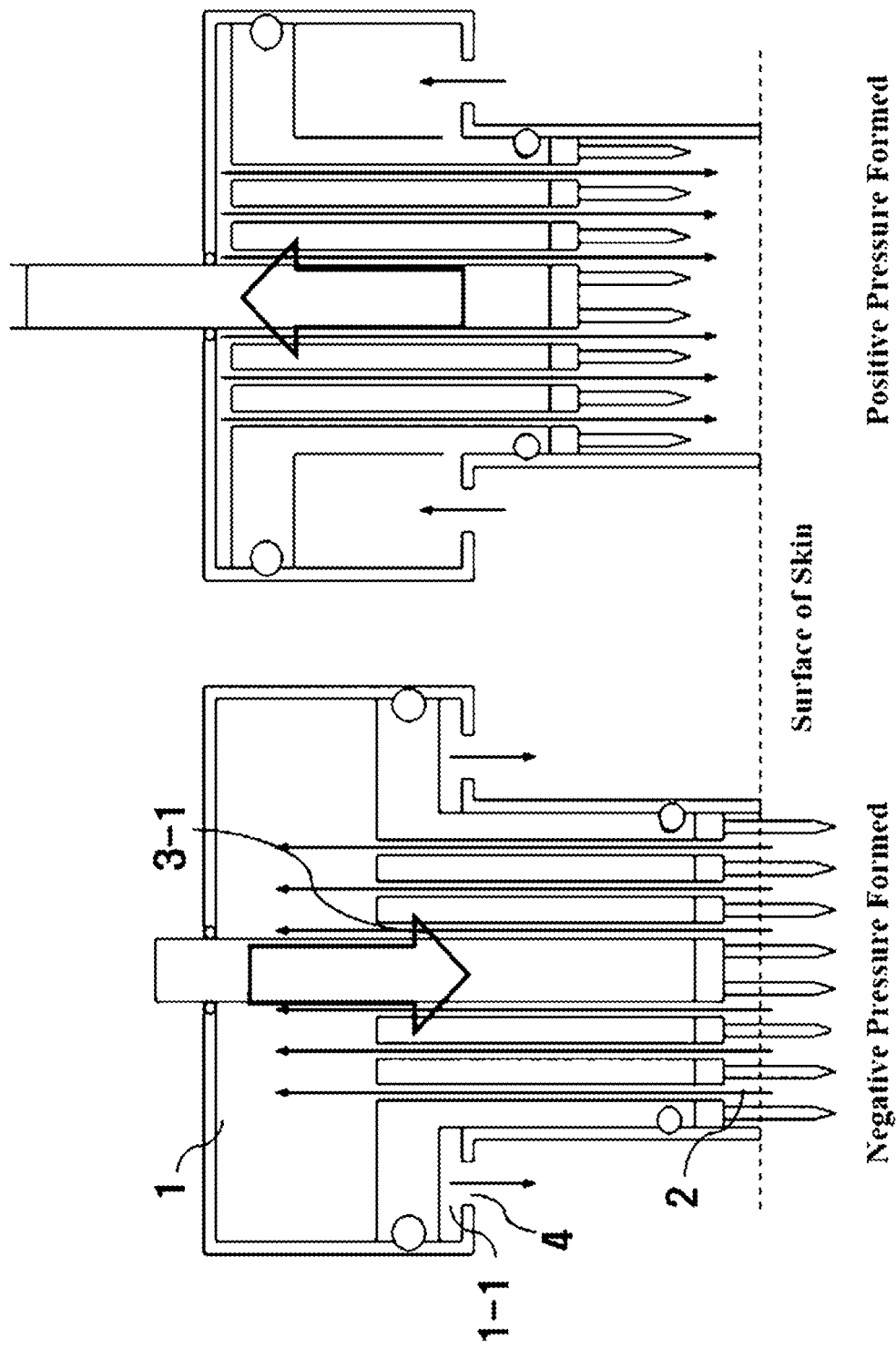
FIG. 5 is a sectional view illustrating a pumping effect made as the medicine injecting tip works, according to the inventive concept.
Figure 6:
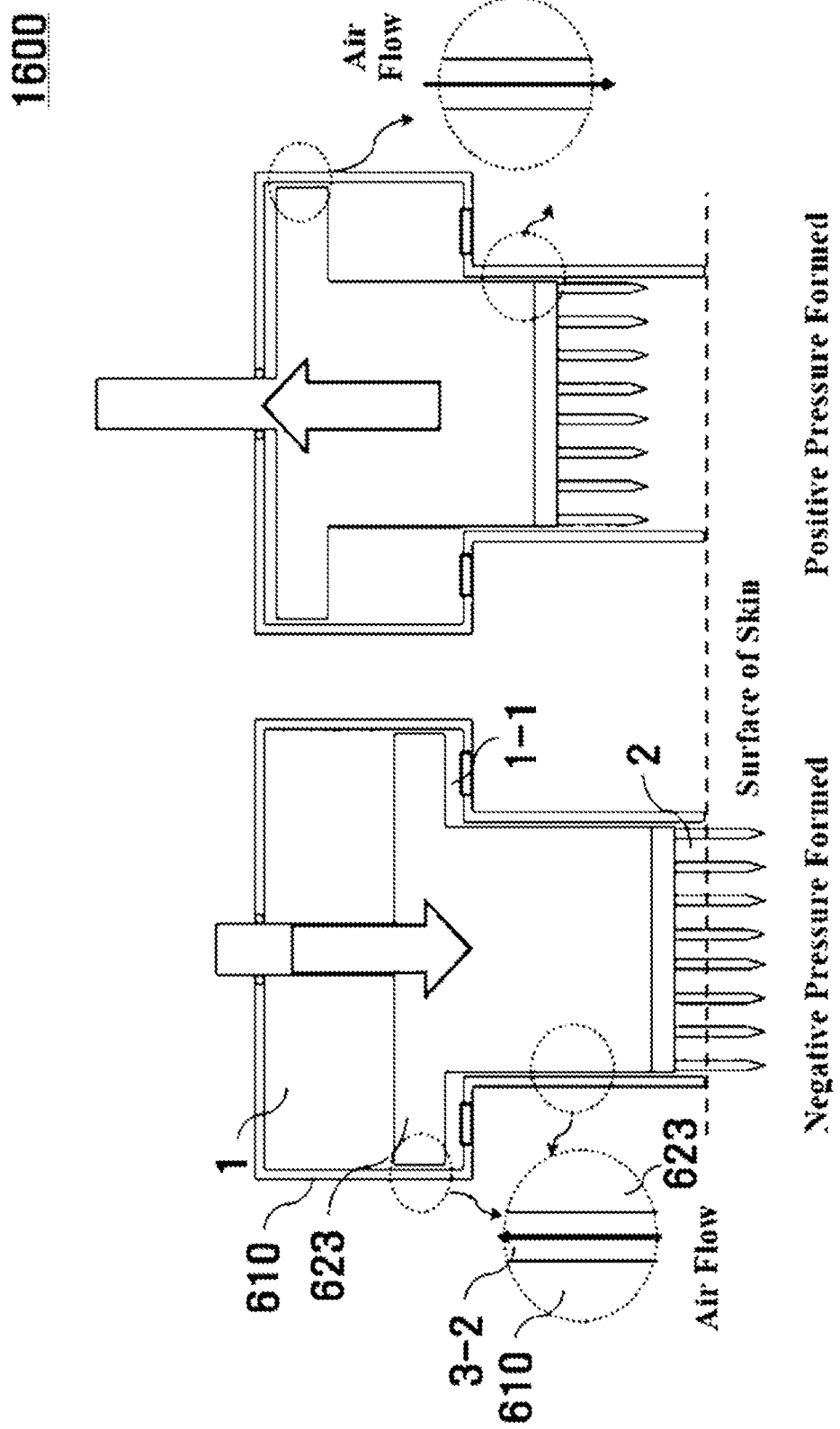
FIG. 6 is a sectional view illustrating a pumping effect made as a medicine injecting tip works, according to a first modification of the inventive concept.
Figure 7:
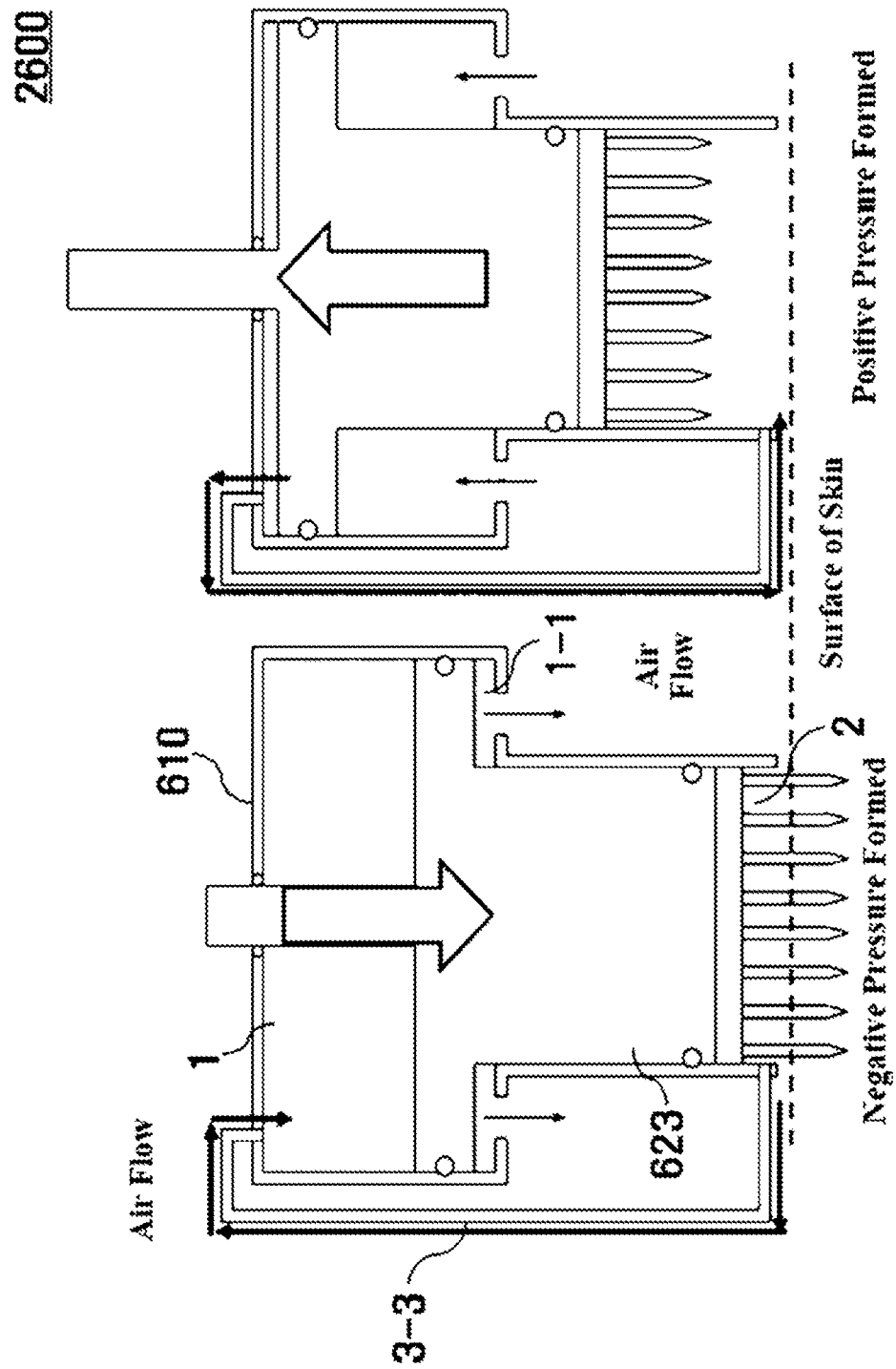
FIG. 7 is a sectional view illustrating a pumping effect made as a medicine injecting tip works, according to a second modification of the inventive concept.
Figure 8:
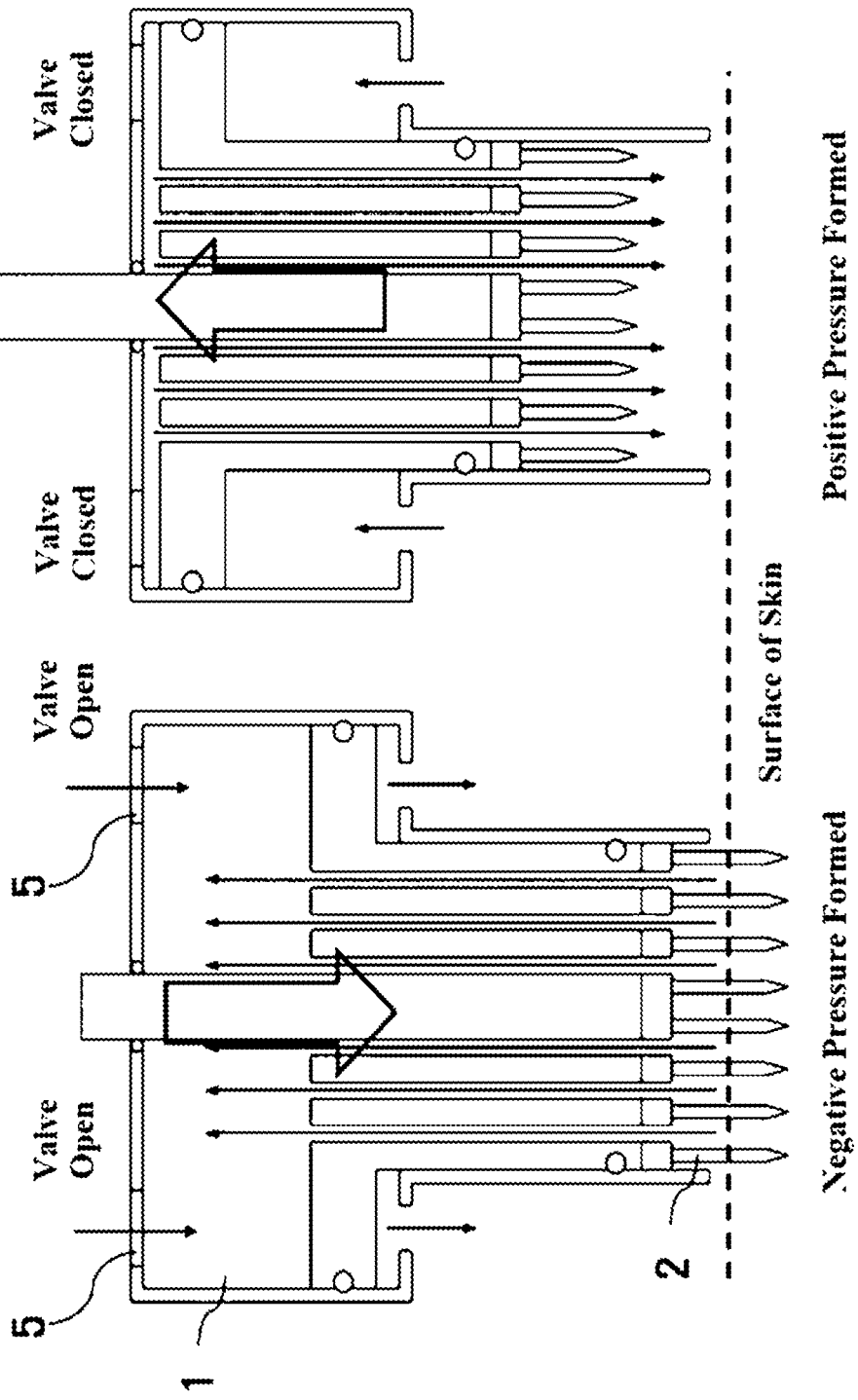
FIG. 8 is a sectional view illustrating a pumping effect made as a medicine injecting tip works, according to a third modification of the inventive concept.
Figure 9:
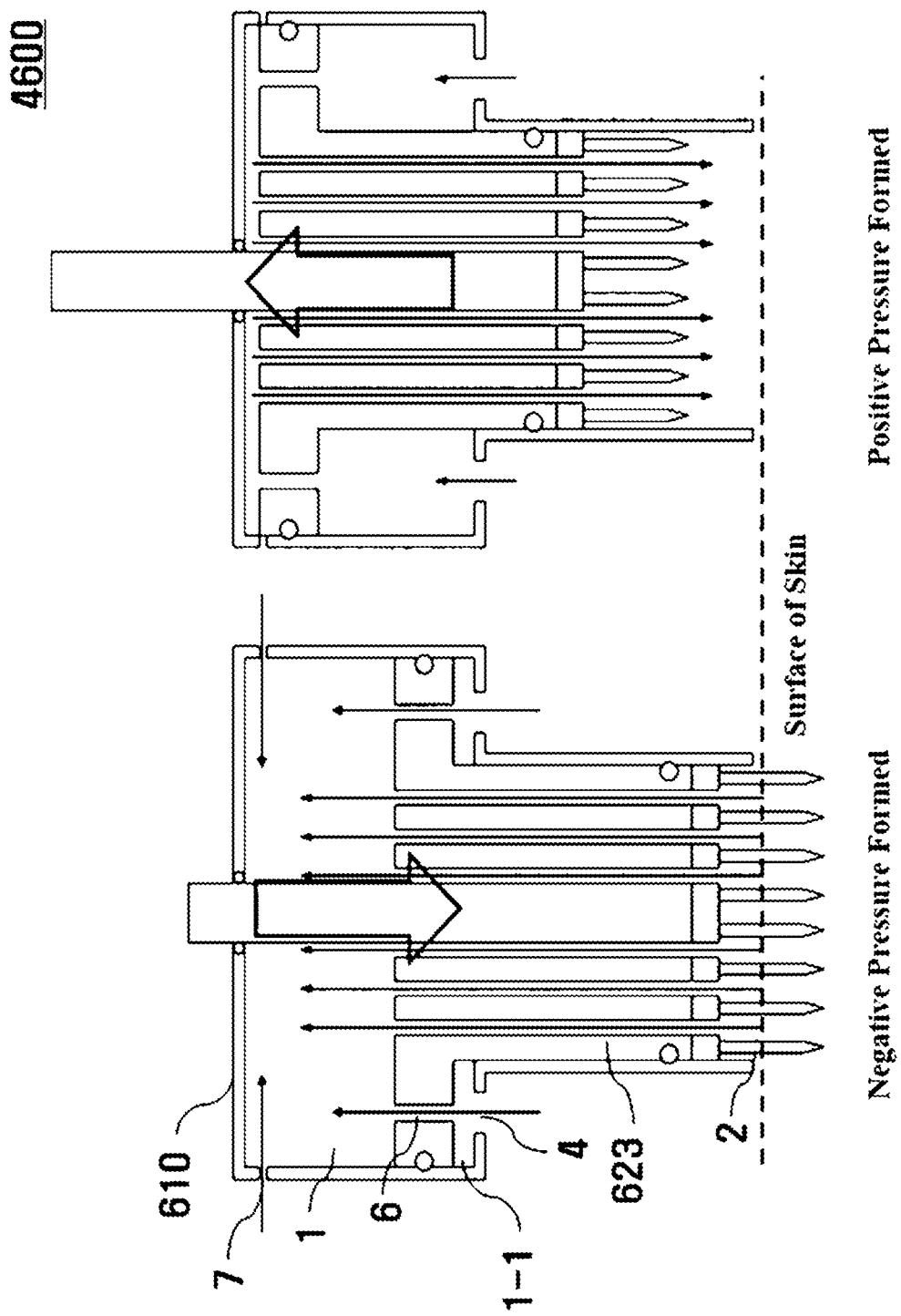
FIG. 9 is a sectional view illustrating a pumping effect made as a medicine injecting tip works, according to a fourth modification of the inventive concept.
Figure 10:
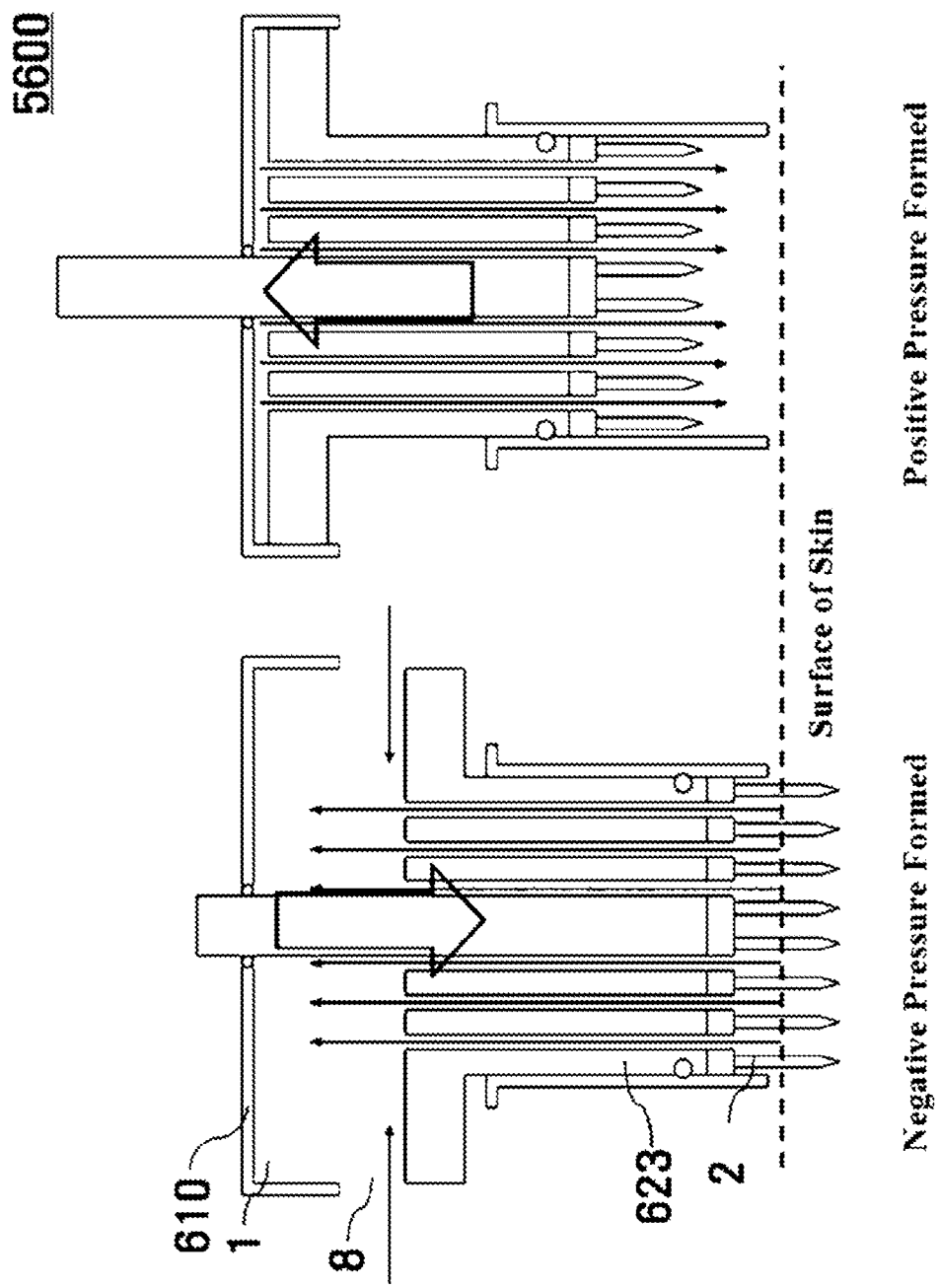
FIG. 10 is a sectional view illustrating a pumping effect made as a medicine injecting tip works, according to a fifth modification of the inventive concept.
Figure 11:
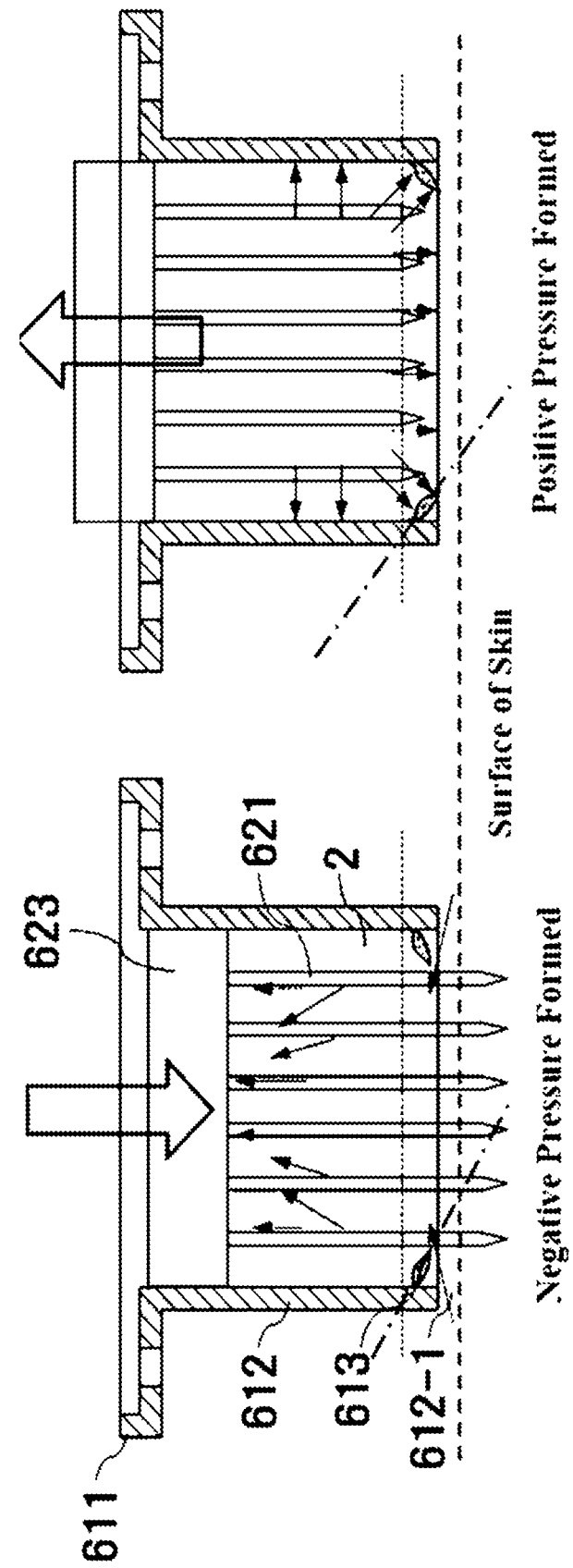
FIG. 11 is a sectional view illustrating a pumping effect improved due to a groove and a seat formed in a second cylinder in a medicine injecting tip according to the inventive concept.

Hereinafter, a skin treating device 1000 according to the inventive concept will be described with reference to accompanying drawings. FIGS. 1A and 1B is a schematic view illustrating that a high frequency is applied using RF needles. FIG. 2 is a perspective view illustrating a skin treating device, according to the inventive concept. FIG. 3 is a perspective view illustrating a hand piece, according to the inventive concept. FIG. 4 is a sectional view illustrating a medicine injecting tip, according to the inventive concept. FIG. 5 is a sectional view illustrating a pumping effect made as the medicine injecting tip works, according to the inventive concept. FIG. 6 is a sectional view illustrating a pumping effect made as a medicine injecting tip works, according to a first modification of the inventive concept. FIG. 7 is a sectional view illustrating a pumping effect made as a medicine injecting tip works, according to a second modification of the inventive concept. FIG. 8 is a sectional view illustrating a pumping effect made as a medicine injecting tip works, according to a third modification of the inventive concept. FIG. 9 is a sectional view illustrating a pumping effect made as a medicine injecting tip works, according to a fourth modification of the inventive concept. FIG. 10 is a sectional view illustrating a pumping effect made as a medicine injecting tip works, according to a fifth modification of the inventive concept. FIG. 11 is a sectional view illustrating a pumping effect improved due to a groove and a seat formed in a second cylinder in a medicine injecting tip according to the inventive concept.

Hereinafter, the term "vertical direction" may be a vertical direction illustrated in FIG. 4, and may be used interchangeably with the term "up-and-down direction". One side in the "vertical direction" may be an upper portion, and another side in the "vertical direction" may be a lower portion.

According to the inventive concept, a skin treating device 1000 may be used for scar treatment, hair growth treatment, osmidrosis treatment, vascular treatment, fat reduction, wrinkle removal, skin elasticity recovery, sebum removal, and acne treatment.

According to the inventive concept, a skin treating device 1000 may include a main body 100, a display module 200, an operating module 300, an electronic control module (not illustrated), a cable 400, a hand piece 500, a medicine injecting tip 600 for injecting a medicine, a driving module 700, and a power supply module (not illustrated).

The main body 100 may include the display module 200 and the operating module 300. The display module 200 may be manufactured in the form of a panel to visually provide various piece of information to a doctor instructing a skin care procedure. Therefore, for example, the display module 200 may display, in the form of a graph, the output level or an impedance of the high frequency applied to a dermal layer of a present target point. In addition, the display module 200 may display an operating mode currently being performed by the skin treating device 1000 according to the inventive concept. In addition, the display module 200 may display biometric information of a deep portion of the skin tissue at the target point.

The operating module 300 may be provided in the form of a button on the outer surface of the main body 100. The doctor may turn on/off the skin treating device 1000 through the operating module 300, select an operating mode of the skin treating device 1000, and change an output level of the high frequency applied to a target point.

Meanwhile, when the display module 200 is provided in the form of a touch screen, at least a portion of the operating module 300 may be omitted. In this case, the doctor may operate the skin treating device by touching a menu displayed on the screen of the display module 200.

An electronic control module (not illustrated) may be embedded in the main body 100 to electronically control components of the skin treating device 1000. To this end, the electronic control module may be electrically connected with the driving module 700 and the power supply module through a cable 400. In other words, the electronic control module may apply a control signal, which corresponds to an operating signal applied by a doctor, to the driving module 700 and the power supply module, in response to the operation signal by the doctor.

For example, a driving period of the driving module 700 may be controlled through a control signal of the electronic control module. Accordingly, the reciprocating driving period of the needle unit 620 of the medicine injecting tip 600 may be controlled.

In addition, the output level of the power module may be controlled through the electronic control signal of the electronic control module. Therefore, the wavelength, direction, and intensity of a current applied to at least one needle 621 of the needle unit 620 may be changed, and thus the output level of the high frequency applied to the target point may be controlled.

Meanwhile, according to the inventive concept, a high frequency does not have to be essentially applied to the at least one needle 621 in the skin treating device 1000. In other words, electric energy may not be applied to the at least one needle 621 based on a treatment purpose, a treatment effect, and an economical effect.

A cable 400 may perform the same function as that of the conductive line to connect the electronic control module with the driving module 700 or to connect the electronic control module with the power module. To this end, the cable 400 may extend to one side from the main body 100 to connect the main body 100 with the hand piece 500. The cable 400 may include a plurality of wires provided therein to form channels depending on types of electrical signals, and the outer skin of the cable 400 and the second cable may insulate and cover a bundle of wires having various channels.

The hand piece 500 is a part held by the doctor. In addition, the doctor may change the target point (e.g., a part of the face) by moving the hand piece 500 in contact with the skin of a target person. The hand piece 500 may be disposed on the cable 400 and may be positioned at an end portion of the cable 400 in the extending direction of the first cable 400.

The hand piece 500 may be provided therein with the driving module 700 and the power supply module. Accordingly, the cable 400 may electrically connect the driving module 700 and the power supply module, which are provided in the hand piece 500, with an electronic control module provided in the main body 100. The medicine injecting tip 600 may be mounted on the end portion of the hand piece 500. In this case, the medicine injecting tip 600 may be mounted on the end portion of the hand piece 500 to be replaceable in the form of a cartridge form.

The hand piece 500 is provided at an outer portion thereof with a first conductive member 501 to electrically the needle unit 620 of the medicine injecting tip 600 with the power supply module and a second conductive member 502 docked on a cable connector 503 to electrically the power module to the cable 400. In this case, the first conductive member 501 and the second conductive member 502 may be manufactured in the form of a film. For example, the first conductive member 501 and the second conductive member 502 may be flexible printed circuit boards (FPCB). The needle unit 620 of the medicine injecting tip 600 reciprocates (drive), which is described below. The conductive line of the needle unit 620 of the medicine injecting tip 600 and the power supply module and the conductive line of the power supply module and the cable 400 may be provided at the outer portion of the hand piece 500 such that the conductive lines are prevented from interrupting the reciprocation of the needle unit 620 of the medicine injecting tip 600.

The medicine injecting tip 600 may be a member to apply a high frequency to the deep portion of the skin at the target point. The medicine injecting tip 600 may be detachably mounted to an end portion of hand piece 500. In other words, the medicine injecting tip 600 of the inventive concept may be manufactured in the form of a cartridge and thus may be replaceable with new one.

The medicine injecting tip 600 may include a cylinder 610 and the needle unit 620. The cylinder 610, which serves as a stator, may be a member detachably mounted on the end portion of the hand piece 500. The needle unit 620, which serves as an actuator (moving in a vertical direction), includes at least one needle 621 to be invaded into the deep portion of the skin at the target point at a specific period (the driving period of the driving module). If necessary, the needle unit 620 may be a member which applies the radio frequency (RF) to the dermal layer of the skin.

The cylinder 610 may be hollowed in the vertical direction. The needle unit 620 may be disposed in the inner space of the cylinder 610. The bottom surface of the cylinder 610 may be open, and the lower end portion of the cylinder 610 may be disposed on the surface of the skin at the target point. Thus, the open portion of the cylinder 610 may be closed by the surface of the skin at the target point.

The cylinder 610 may include a first cylinder 611 and a second cylinder 612. In this case, the first cylinder 611 may be positioned at an upper portion of the cylinder 610, and the second cylinder 612 may be positioned at the lower portion of the cylinder 610. The lower end portion of the first cylinder 611 and the upper end portion of the second cylinder 612 may be connected with each other. The bottom surface of the second cylinder 612 may be open.

The needle unit 620 may be disposed inside the first cylinder 611 and the second cylinder 612, and the connecting portion between the first cylinder 611 and the second cylinder 612 is closed by the needle unit 620.

A connecting rod 625 of the needle unit 620 may pass through the top surface of the first cylinder 611. In the first cylinder 611, a first space 1 and a redundant space 1-1 may be formed by the first plunger 623-1 of the needle unit 620. In other words, the inner space of the first cylinder 611 may be closed in the vertical direction by the first plunger 623-1 of the needle unit 620, and may be divided into the first space 1 positioned at the upper portion thereof and the redundant space 1-1 positioned at the lower portion thereof.

To maintain the airtightness of the first space 1 of the first cylinder 611, a gasket 626 may be disposed between a top surface of the first cylinder 611 and the connecting rod 625 of the needle unit 620. In addition, the gasket 626 may be interposed between the inner circumferential surface of the first cylinder 611 and the outer circumferential surface of the first plunger 623-1 of the needle unit 620.

The lower end portion of the second cylinder 612 may be disposed on the surface of the skin at the target point. Thus, the open portion of the bottom surface of the second cylinder 612 may be closed by the surface of the skin of the target point. The second cylinder 612 may have a second space 2 having a bottom surface open by the second plunger 623-2 of the needle unit 620. The inner space of the second cylinder 612 may be closed in the vertical direction by the second plunger 623-2 of the needle unit 620, and provided at an upper portion thereof with a holder 622 of the needle unit 620 and the second plunger 623-2 of the needle unit 620, and provided at a lower portion thereof with the second space 2 having a bottom surface which is open.

One or more grooves 612-1 may be formed in the bottom surface of the second cylinder 612 (see FIG. 3). The one or more grooves 612-1 of the second cylinder 612 may be formed from an inner circumferential surface of the second cylinder 612 to the outer circumferential surface of the second cylinder 612. In other words, the one or more grooves 612-1 of the second cylinder 612 may be formed through the second cylinder 612. In addition, the at least one or more grooves 612-1 of the second cylinder 612 may be arranged to be spaced apart from each other along the circumference of the bottom surface of the second cylinder 612. In other words, the one or more grooves 612-1 of the second cylinder 612 may be formed to be spaced apart from each other in the circumferential direction.

Meanwhile, as described above, the open portion of the bottom surface of the second space 2 may be closed by the surface of the skin at the target point. In this case, to maintain the airtightness of the second space 2, the gasket 626 is interposed between the inner circumferential surface of the second cylinder 612 and the outer circumferential surface of the second plunger 623-2 of the needle unit 620. Meanwhile, in the state that the airtightness of the second space 2 is maintained, only the lower end portion of the second space 2 is selectively connected with the outside by one or more grooves 612-1 of the second cylinder 612, to increase the pumping effect described later.

One or more needles 621 of the needle unit 620 may be disposed in the second space 2. As described above, since the bottom surface of the second space 2 is open, the one or more needles 621 may enter the surface of the skin at the target point through the open portion of the second space 2.

The sectional area, which is perpendicular to the vertical direction, of the first cylinder 611 may be larger than the sectional area, which is perpendicular to the vertical direction, of the second cylinder 612. Therefore, as the plunger 623 of the needle unit 620 reciprocates in the vertical direction, the variation in the volume of the first space 1 of the first cylinder 611 is greater than the variation in the volume of the second space 2 of the second cylinder 612

The cylinder 610 may further include a seat 613 (see FIG. 11). The seat 613 may be positioned in the second space 2. The seat 613 may be disposed to be inclined inward and downward from the inner circumferential surface of the second cylinder 612. The seat 613 may be disposed in a ring shape along the inner circumferential surface of the second cylinder 612. In this case, according to the inventive concept, the seat 613 may be disposed along the circumference of one or more needles 621 of the needle unit 620, similarly to the form of a "valve seat". In other words, the seat 613 may cover the circumference of one or more needles 621 of the needle unit 620.

The outer end portion of the seat 613 may be a fixed end, and the inner end portion of the seat 613 may be a free end. Therefore, the downward inclination angle of the seat 613 may be varied by the flow of air around the seat 613. To improve the variable action of the inclination angle, the seat 613 may be formed of an elastic material.

The outer end of the seat 613 may be disposed above the one or more grooves 612-1 of the second cylinder 612. As a result, the inclination angle of the seat 613 may vary depending on the flow of air flowing through the one or more grooves 612-1 of the second cylinder 612. The seat 613 may interact with one or more grooves 612-1 of the second cylinder 612 to increase the pumping effect described below.

The needle unit 620 may be disposed in the cylinder 610. The needle unit 620 may reciprocate in the vertical direction by the driving module 700. In other words, the needle unit 620 may be disposed inside the first cylinder 611 and the second cylinder 612, and may reciprocate like a "piston". In addition, the plunger 623 may be provide to divide the inner surface of the first and second cylinders 611 and 612, and may vary the volume of the inner space of the first cylinder 611 and the second cylinder 612.

In addition, the needle unit 620 may generate a high frequency in the deep portion of the skin at the target point, and may recover the collagen and the elastic fiber, which are damaged by the thermal energy of the high frequency, over time so the elasticity of the skin may be increased.

The needle unit 620 may include one or more needles 621, the holder 622, the plunger 623, and the connecting rod 625.

As the one or more needles 621 may reciprocate together with the plunger 623, the one or more needles 621 may be alternately inserted into or discharged from the skin. The high frequency is applied to the one or more needles 621 such that thermal energy is generated in the deep portion of the skin at the target point.

However, the inventive concept is not limited thereto, and one or more needles 621 may be applied with electric energy and ultrasonic waves having various wavelength bands in addition to the high frequency. Furthermore, as described above, the electrical energy or ultrasonic wave may not be applied to one or more needles 621.

When electrical energy such as a high frequency is applied to the one or more needles 621, the one or more needles 621 are electrically connected with the power supply module to receive power. To this end, the one or more needles 621 may be electrically connected with the power supply module by the first conductive member 501 described above.

Meanwhile, the one or more needles 621 may be a bipolar type electrode unit in which a plurality of electrodes have two polarities, and a high frequency is generated between neighboring electrodes, and or a monopolar type electrode unit in which all of the plurality of electrodes have the same polarity. Meanwhile, when the one or more needles 621 is in a monopolar type, a ground electrode module (not illustrated) may be additionally provided to reflux the high frequency generated from the one or more needles 62.

The one or more needles 621 may be supported by the holder 622. The one or more needles 621 may extend downward in the holder 622. The one or more needles 621 may be disposed in the second space 2 of the second cylinder 612.

The one more needles 621 may reciprocate in the vertical direction by the driving force of the driving module 700. The lower end portions of the one or more needles 621 at the bottom dead center may be disposed on the deep portion of the skin at the target point, and the lower end portions of the one or more needles 621 at the top dead center may be disposed on the surface of the skin at the target point.

Thus, the one or more needles 621 may be repeatedly invaded into the deep portion of the skin at the target point. In this case, the one or more needles 621 may protrude downward through the open portion formed in the bottom surface of the second space 2 of the second cylinder 612 and then return upward. Meanwhile, the depth of invasion of the one or more needles 621 may be approximately 2.1 mm.

The holder 622 may be a member supporting the one or more needles 621. The holder 622 may be disposed in the second space 2 of the second cylinder 612, similarly to the one or more needles 621. In addition, the holder 622 may be disposed on the bottom surface of the second plunger 623-2, and may be coupled to the second plunger 623-2. Furthermore, if necessary, the holder 622 may be omitted. In this case, one or more needles 621 may be disposed directly on the plunger 623.

The plunger 623 may reciprocate downward or upward to form the first space 1 and the second space 2 in the cylinder 610. In addition, a first channel 3 connecting the first space 1 with the second space 2 may be formed in the plunger 623.

The variation in the volume of the first space 1 is greater than the variation in the volume of the second space 2 in the reciprocating movement of the plunger 623, so the gas in the second space 2 may move into the first space 1 through the first channel 3 when the plunger 623 moves downward, and the gas in the first space 1 may move into the second space 2 through the first channel 3 when the plunger 623 moves upward.

Accordingly, the one or more needles 621 are invaded into the skin, and a negative pressure state may be formed in the second space 2 (pressure is decreased) when the plunger 623 moves downward. When the plunger 623 moves upward, the one or more needles 621 are discharged from the skin, and a positive pressure state may be formed in the second space 2 (pressure is increased).

The plunger 623 may include the first plunger 623-1 and the second plunger 623-2. The first plunger 623-1 may be disposed in an inner space of the first cylinder 611. The first plunger 623-1 closes the inner space of the first cylinder 611 in the vertical direction, and may form the first space 1 positioned at the upper portion of the first cylinder 611 and the redundant space positioned at the lower portion of the first cylinder 611.

The first plunger 623-1 may reciprocate in the vertical direction by the driving force of the driving module 700. When the first plunger 623-1 moves downward, the volume of the first space 1 may be increased, and the volume of the redundant space 1-1 may be decreased (see FIG. 5). When the first plunger 623-1 moves upward, the volume of the first space 1 may be decreased, and the volume of the redundant space 3 may be increased (see FIG. 5).

The second plunger 623-2 may be positioned in the inner space of the second cylinder 612. The second plunger 623-2 may close the inner space of the second cylinder 612 in the vertical direction to form the second space 2 in the second cylinder 612.

The second plunger 623-2 may reciprocate in the vertical direction by the driving force of the driving module 700. When the second plunger 623-2 moves downward, the volume of the second space 2 may be decreased (see FIG. 5). When the second plunger 623-2 moves upward, the volume of the second space 2 may be increased (see FIG. 5).

The first channel 3 connecting the first space 1 with the second space 2 may be formed in the first plunger 623-1 and the second plunger 623-2. In this case, the first channel 3 formed in the first plunger 623-1 and the second plunger 623-2 may be one or more fluid passages 3-1 passing through (formed through) the first plunger 623-1 and the second plunger 623-2 in the vertical direction.

The connecting rod 625 may be disposed at an upper portion of the first plunger 623-1. The connecting rod 625 may move in the vertical direction by the driving force of the driving module 700. The connecting rod 625 may be connected to the driving module 700 and the first plunger 623-1 to transmit a driving force of the driving module 700 to the first plunger 623-1.

Hereinafter, the operation (pumping effect) of the medicine injecting tip 600 will be described with reference to FIG. 5. When the skin treating device 1000 of the inventive concept is operated, the needle unit 620 may reciprocate in the vertical direction (up-down direction), and may repeatedly invade the skin at the target point (when a high frequency is applied, thermal energy is generated in the deep portion of the skin). Meanwhile, a medicine may be applied to the surface of the skin at the target point to alleviate the pain caused by invasion or to promote the regeneration of the wound.

When the needle unit 620 moves downward, the volume of the first space 1 may be increased and the volume of the second space 2 may be decreased. In this case, the variation in the volume of the first space 1 may be greater than the variation in the volume of the second space 2 due to the difference in the sectional area, which are perpendicular to the vertical direction, between the first space 1 and the second space 2. In other words, the increment in the volume of the first space 1 may be greater than the decrement in the volume of the second space 2. Meanwhile, since the first space 1 and the second space 2 are connected with each other through the first channel 3, the gas in the second space 2 may move into the first space 1 through the first channel 3 (see FIG. 5; the movement of the gas due to the pressure difference resulting from the difference between volume variations). Thus, the second space 2 is in a "negative pressure state (pressure decreased; to the contrary, the first space is in a positive pressure state as pressure is increased)" to suction the surface of the skin at the target point, and the height of the skin of the surface at the target point is made uniform. Accordingly, the one or more needles 621 may be invaded into the skin to a uniform depth (the invasion effect to the uniform depth; all the plurality of needles irradiate a high frequency at the invasion depth (preset depth) satisfying the medical design condition)

When the needle unit 620 moves upward, the volume of the first space 1 may be decreased and the volume of the second space 2 may be increased. In this case, the variation in the volume of the first space 1 may be greater than the variation in the volume of the second space 2 due to the difference in the sectional area, which are perpendicular to the vertical direction, between the first space 1 and the second space 2. In other words, the increment in the volume of the first space 1 may be greater than the decrement in the volume of the second space 2 of the second cylinder 612. Meanwhile, since the first space 1 and the second space 2 are connected with each other through the first channel 3, the gas in the first space 1 may move into the second space 2 through the first channel 3 (see FIG. 5; the movement of the gas due to the pressure difference resulting from the difference between volume variations). Thus, the second space 2 is in a "positive pressure state (pressure increased; to the contrary, the first space is in a negative pressure state as pressure is decreased)", so the medicine applied to the surface of the skin at the target point is deeply injected into the invasion part (a hole formed as the needle electrode is inserted and discharged) (an effect of deeply injecting the medicine into the deep portion of the skin)

Meanwhile, a second channel 4 connecting the redundant space 1-1 with the outside may be formed in the first cylinder 611. The second channel 4 may prevent the pressure of the gas in the redundant space 1-1 from interfering with the reciprocating movement of the first plunger 623-1 in the vertical direction. In other words, when the needle unit 620 moves downward, air in the redundant space 1-1 may flow out to remove the resistance.

Hereinafter, a medicine injecting tip 1600 according to the first modification of the inventive concept and a medicine injecting tip 2600 according to the second modification of the inventive concept will be described with reference to FIGS. 6 and 7. The first channel 3 according to the inventive concept may have various shapes in addition one or more fluid passages 3-1 formed in the above-described plunger 623.

As illustrated in FIG. 6, in the medicine injecting tip 1600 of the first modification of the inventive concept, the first channel 3 has a gap 3-2 between the cylinder 610 and the plunger 623. In this case, according to the inventive concept, it may be preferred that the above-described second channel 4 is not formed. Alternatively, the gasket 626 between the cylinder 610 and the plunger 623 may be omitted or the gap 3-2 between the cylinder 610 and the plunger 623 may be formed in the gasket 626 between the cylinder 626 and the plunger 623.

In addition, as illustrated in FIG. 7, in the medicine injecting tip 2600 according the second modification of the inventive concept, the first channel 3 may be a tube 303 connecting the first space 1 and the second space 2. In other words, in the second modification of the inventive concept, the first channel 3 is provided as a separate member.

Meanwhile, according the inventive concept, the shape of the first channel 3 may be a combination (at least one) of the flow path 3-1, the gap 3-2, and the tube 3-3.

Hereinafter, a medicine injecting tip 3600 according to the third modification of the inventive concept, a medicine injecting tip 4600 according to the fourth modification of the inventive concept, and a medicine injecting tip 5600 according to the fifth modification of the inventive concept will be described with reference to FIGS. 8, 9, and 10. The third to fifth modifications of the inventive concept relate to that the higher positive pressure state is formed in the second space 2 of the inventive concept.

To this end, a valve 5 is provided in the medicine injecting tip 3600 according to the third modification of the inventive concept. The valve 5 may connect the outside and the first space 1 in the open state. In addition, the valve 5 may be open when the plunger 623 moves downward (open in a negative pressure state of the first space), thereby allowing external air to flow into the first space 1. To the contrary, the valve 5 may be closed (closed in a positive pressure state of the first space) when the plunger 623 moves upward, thereby preventing air from flowing out of the first space 1. Accordingly, when the plunger 623 moves down, air introduced from the outside is additionally accumulated in the first space 1. When the plunger 623 moves up, the external air additionally accumulated in the first space moves into the second space 2 to increase the positive pressure of the second space 2 (the medicine is increasingly injected due to the pumping effect).

Meanwhile, the opening and closing of the valve 5 is not limited to being driven by electric, but may be driven automatically. For example, when the valve 5 which is structurally open only in one direction (the direction in which external air is introduced the first space) is used, the valve 5 may be automatically open only in the negative pressure state of the first space 1.

In addition, in a medicine injecting tip 4600 according to the fourth modification of the inventive concept, at least one of a third channel 6 connecting the first space 1 and the redundant space 1-1, or the fourth space 7 connecting the first space 1 with the outside may be formed. In this case, as in the third modification of the inventive concept, when the plunger 623 moves downward, external air may be introduced into the first space 1 through the third channel 6 and the fourth channel 7 and accumulated. When the plunger 623 moves upward, the external air accumulated in the first space moves into the second space 2 to increase the positive pressure of the second space 2 (the medicine is increasingly injected due to the pumping effect).

Meanwhile, the fourth channel 7 is open without being overlapped with the plunger 623 (especially, the first plunger) when the plunger 623 moves down. When the plunger 623 moves up, the fourth channel 7 is overlapped with the plunger 623 (especially, the first plunger) to be closed (open or closed due to the movement of the plunger).

This is to fully move the air in the first space 1 into the second space 2 by preventing the air from leaking out of the first space 1 when the plunger 623 moves up. Differently, when the plunger 623 moves up, since external air is introduced into the redundant space 1-1, the leakage of the external air through the third channel 6 may be slight even if the third channel 6 is not closed.

In addition, in a medicine injecting tip 5600 according to the fifth modification of the inventive concept, a fifth channel 8 connecting the outside with the first space 1 may be formed instead of the redundant space 1-1, which is different from the medicine injecting tip 600 described above.

The fifth channel 8 is open as the plunger 623 moves and allows external air to be accumulated in the first space 1, when the plunger 623 moves down. When the plunger 623 moves up, the fifth channel 8 is closed as the plunger 623 move, such that the air in the first space 1 is fully moved into the second space 2, thereby increasing the positive pressure of the second space 2 (the medicine is increasingly injected due to the pumping effect).

Meanwhile, it should be noticed by those skilled in the art that the above-described technical features according to the inventive concept and the technical features of the first to fifth modifications may be combined within a technical scope of the inventive concept.

The driving module 700 may be provided in the hand piece 500 and may provide driving force for reciprocating the needle unit 620 of the medicine injecting tip 600. Various type of driving devices may be used as the driving device of the driving module 700. As an example, the driving module 700 may include a pneumatic cylinder or may include a linear motor.

The power supply module may be provided in the hand piece 500 and may supply power to one or more needles 621. In this case, the power supply module may supply DC power or AC power to the one or more needles 621. The power supply module may be electrically connected with the one or more needles 621 through the first conductive member 501, and may be electrically connected with the cable 400 through the second conductive member 502. Accordingly, the power supply module may receive a control signal of the electronic control module through the cable 400 and apply power corresponding thereto to the one or more needles 621

The following description will be made with reference to FIG. 11 regarding that the pumping effect of the medicine injecting tip 600 is improved. when one or more grooves 612-1 are formed and a seat 613 is added in the second cylinder 612.

When the needle unit 620 moves down, external gas is introduced into the second space 2 and moved into the first space 1 through one or more grooves 612-1 of the second cylinder 612. The seat 613 is pushed upward due to the flow of the external gas, so the downward inclination angle may be reduced. Therefore, the seat 613 does not block the flow of the external gas introduced through the one or more grooves 612-1 of the second cylinder 612. Accordingly, the flow of the gas from the second space 2 to the first space 1 is accelerated by the flow of the external gas (the gas in the second space is pushed by the flow of the external gas and more rapidly moved into the first space), thereby improving the pumping effect (see FIG. 11).

When the needle unit 620 moves up, the seat 613 is pushed downward by the flow of the gas in the second space 2, so the downward inclination angle may be increased. Accordingly, the seat 613 may block the gas in the second space 2 from being discharged to the outside through the one or more grooves 612-1 of the second cylinder 612. Accordingly, the positive pressure formed in the second space 2 is increased (the external gas having moved into the first space when the needle unit is moved downward is moved again into the second space when the needle unit is moved upward and blocked from being discharged to the outside, thereby increasing the positive pressure), thereby improving the pumping effect (see FIG. 11).

Hereinafter, a method for treating a skin using the medicine injecting tip 600 according to the inventive concept will be described with reference to FIG. 12.

According to the inventive concept, the method for treating the skin may include forming a negative pressure state in the second space 2 by moving downward one or more needles 621 and a plunger 623 (needle electrode inserted) (S100); applying, by the one or more needles 621, a high frequency to a deep portion of a skin at a target point (S200); and forming a positive pressure state in the second space 2 by moving the one or more needles 621 and the plunger 623 upward (needle discharged) (S300).

In the forming of the negative pressure state in the second space 2 (S100), the one or more needles 621 is inserted into the skin, and the surface of the skin is pulled to the second space 2 as the second space 2 is in the negative pressure state, such that the surface of the skin may be uniformly provided. Accordingly, one or more needles 621 may be invaded to a preset depth, and the treatment effect may be improved.

In the applying, by the one or more needles 621, the high frequency to the deep portion of the skin (S200), thermal energy may be generated into the deep portion of the skin to remove the waste tissue of the skin (skin regeneration and healing effect).

In addition, in the forming of the positive pressure state in the second space 2 (S300), the one or more needles 621 are discharged from the skin such that the medicine is injected into the hole formed in the skin. The hole may be formed in the skin as the one or more needles 621 are inserted and discharged, and the medicine may be injected into the hole formed in the skin when the second space 2 is the positive pressure state.

At the initial stage of the forming a positive pressure state in the second space 2 by moving the one or more needles 621 and the plunger 623 upward (S300), the second space 2 is set to be in the negative pressure state (the negative pressure state formed in S100), so the hole formed in the skin may be spread. Thereafter, when the positive pressure state is formed in the second space 2, the medicine is injected into the spread hole in the state of receiving pressure, such that the medicine is deeply injected.

According to the inventive concept, the medicine may be injected into the hole formed in the surface of the skin by the needle in the positive pressure state and the skin is pulled in the negative pressure state, so the needle may be inserted to a preset depth.

Further, according to the inventive concept, the hand piece equipped with the medicine injecting tip and the skin treating device using the medicine injecting tip are provided.

The effects of the inventive concept are not limited to the above, but other effects, which are not mentioned, will be apparently understood to those skilled in the art.

Although embodiments of the inventive concept have been described with reference to accompanying drawings, those skilled in the art should understand that various modifications are possible without departing from the technical scope of the inventive concept or without changing the subject matter of the inventive concept. Therefore, those skilled in the art should understand that the technical embodiments are provided for the illustrative purpose in all aspects and the inventive concept is not limited thereto.

What is claimed is:

1. A medicine injecting tip, comprising:
a cylinder;
medicine;
a plunger provided in the cylinder, wherein the plunger is configured to reciprocate based on a driving force provided by a driving device; and
a needle disposed in the plunger, wherein the needle is configured to form a hole in skin of a patient based on the needle being inserted into and discharged from the skin of the patient, wherein upward movement of the plunger within the cylinder is configured to discharge the needle from the hole and to form positive pressure around the hole, causing the medicine to be injected into the hole.

2. The medicine injecting tip of claim 1, wherein the cylinder comprises a first space and a second space, and wherein the needle is disposed in the second space.

3. The medicine injecting tip of claim 2, wherein downward movement of the plunger within the cylinder is configured to form a negative pressure state in the second space.

4. The medicine injecting tip of claim 3, wherein forming the negative pressure state causes a surface of the skin to be pulled to the second space such that the needle is inserted into the skin to a preset depth.

5. The medicine injecting tip of claim 2, wherein the plunger comprises a first channel, which penetrates the plunger in a direction that the plunger reciprocates, connects the first space with the second space, and is configured to transfer air from the first space to the second space.

6. The medicine injecting tip of claim 5, wherein the first channel comprises at least one of:
a fluid passage formed in the plunger,
a gap between the cylinder and the plunger, or
a tube connecting the first space with the second space.

7. The medicine injecting tip of claim 5, wherein reciprocation of the plunger is configured to cause a variation in a volume of the first space which is greater than or equal to a variation in a volume of the second space.

8. The medicine injecting tip of claim 5, wherein a valve is disposed in the cylinder, wherein in an open state, the valve connects the first space to a space outside the medicine injecting tip.

9. The medicine injecting tip of claim 8, wherein the valve, in the open state, is configured to introduce external air into the first space, and wherein the valve, in a closed state, is configured to block air in the first space from leaking outside.

10. The medicine injecting tip of claim 8, wherein the valve is configured to be in the open state when the plunger moves downward and in a closed state when the plunger moves upward.

11. The medicine injecting tip of claim 5, wherein the cylinder includes a first cylinder and a second cylinder;
wherein the plunger includes: a first plunger; and a second plunger;
wherein the first space is positioned between a top wall of the first cylinder and the first plunger, and the second space is an interior section of the second cylinder where the second plunger reciprocates; and
wherein a second channel is formed in the first cylinder to connect a redundant space formed between a bottom wall of the first cylinder and the first plunger with a space outside the medicine injecting tip.

12. The medicine injecting tip of claim 5, wherein the cylinder includes a first cylinder and a second cylinder;
wherein the plunger includes a first plunger and a second plunger;
wherein the first space is positioned between a top wall of the first cylinder and the first plunger, and the second space is an interior section of the second cylinder where the second plunger reciprocates; and
wherein a third channel is formed in the first plunger to connect a redundant space formed between a bottom wall of the first cylinder and the first plunger with the first space.

13. The medicine injecting tip of claim 5, wherein a fourth channel is formed in the cylinder to connect the first space with a space outside the medicine injecting tip.

14. The medicine injecting tip of claim 13, wherein the downward movement of the plunger is configured to open the fourth channel, and the upward movement of the plunger is configured to close the fourth channel.

15. The medicine injecting tip of claim 2, wherein the needle is configured to conduct a radio frequency signal applied through the needle.

16. The medicine injecting tip of claim 1, wherein the driving device includes a pneumatic cylinder or a motor.

17. A hand piece, comprising:
a medicine injecting tip, comprising:
a cylinder;
medicine;
a plunger provided in the cylinder, wherein the plunger is configured to reciprocate; and
a needle disposed in the plunger, wherein the needle is configured to form a hole in skin of a patient based on the needle being inserted into and discharged from the skin of the patient, wherein upward movement of the plunger within the cylinder is configured to discharge the needle from the hole and to form positive pressure around the hole, causing the medicine to be injected into the hole; and
a driving device, wherein the driving device is configured to provide a driving force for reciprocation of the plunger.

18. The hand piece of claim 17, wherein the driving device includes a pneumatic cylinder or a motor.

19. A skin treatment system, comprising:
a console; and
a hand piece connected to the console, wherein the hand piece comprises a detachable medicine injecting tip;
wherein the medicine injecting tip comprises:
a cylinder;
medicine;
a plunger provided in the cylinder, wherein the plunger is configured to reciprocate; and
a needle disposed in the plunger, wherein the needle is configured to form a hole in skin of a patient based on the needle being inserted into and discharged from the skin of the patient, wherein upward movement of the plunger within the cylinder is configured to discharge the needle from the hole and to form positive pressure around the hole, causing the medicine to be injected into the hole;
wherein the hand piece comprises a driving device, wherein the driving device is configured to provide a driving force for reciprocation of the plunger.

20. The system of claim 19, wherein the driving device includes a pneumatic cylinder or a motor.

\* \* \* \* \*

UNITED STATES PATENT AND TRADEMARK OFFICE
CERTIFICATE OF CORRECTION

| | |
|---|---|
| PATENT NO. | : 12,102,811 B2 |
| APPLICATION NO. | : 17/826737 |
| DATED | : October 1, 2024 |
| INVENTOR(S) | : Kyoung Ho An |

It is certified that error appears in the above-identified patent and that said Letters Patent is hereby corrected as shown below:

In the Claims

Claim 11: Column 15, Line 60: "wherein the plunger includes: a first plunger; and a second" should read -- wherein the plunger includes a first plunger and a second --.

Signed and Sealed this
Nineteenth Day of November, 2024

Katherine Kelly Vidal
*Director of the United States Patent and Trademark Office*